(12) United States Patent
Kaib et al.

(10) Patent No.: US 10,269,227 B2
(45) Date of Patent: *Apr. 23, 2019

(54) SYSTEM AND METHOD FOR ADAPTING ALARMS IN A WEARABLE MEDICAL DEVICE

(71) Applicant: ZOLL Medical Corporation, Chelmsford, MA (US)

(72) Inventors: Thomas E. Kaib, Irwin, PA (US); Shane S. Volpe, Saltsburg, PA (US); John G. Clark, Pittsburgh, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/965,287

(22) Filed: Apr. 27, 2018

(65) Prior Publication Data

US 2018/0315286 A1   Nov. 1, 2018

Related U.S. Application Data

(63) Continuation of application No. 15/483,203, filed on Apr. 10, 2017, now Pat. No. 9,990,829, which is a (Continued)

(51) Int. Cl.
*G08B 19/00* (2006.01)
*G08B 21/04* (2006.01)
(Continued)

(52) U.S. Cl.
CPC .......... *G08B 21/0453* (2013.01); *A61B 5/746* (2013.01); *A61N 1/08* (2013.01);
(Continued)

(58) Field of Classification Search
CPC ................... A61N 1/00; A61B 1/00
See application file for complete search history.

(56) References Cited

U.S. PATENT DOCUMENTS

| 3,922,665 A | 11/1975 | Curry et al. |
| 4,094,310 A | 6/1978 | McEachern et al. |

(Continued)

FOREIGN PATENT DOCUMENTS

| DE | 2644236 | 4/1981 |
| EP | 0295497 | 7/1990 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/ull/166/1/111.

(Continued)

*Primary Examiner* — Shirley Lu
(74) *Attorney, Agent, or Firm* — Finch & Maloney PLLC

(57) ABSTRACT

According to another example, a wearable medical device controller is provided. The device controller includes a memory and a processor coupled to the memory. The processor is configured to determine a correlation between a phenomenon identifiable by the wearable medical device controller and at least one response pattern associated with a patient and store, responsive to detecting the correlation, an adaptation path to address the at least one response pattern, the adaptation path specifying an adaptation of at least one characteristic of an alarm. The at least one response pattern may include a plurality of response patterns and the adaptation path may reflect adaptations made to address at least some of the plurality of response patterns.

20 Claims, 5 Drawing Sheets

Related U.S. Application Data continuation of application No. 15/159,557, filed on May 19, 2016, now Pat. No. 9,659,475, which is a continuation of application No. 14/704,033, filed on May 5, 2015, now Pat. No. 9,378,637, which is a continuation of application No. 13/428,703, filed on Mar. 23, 2012, now Pat. No. 9,135,398.

(60) Provisional application No. 61/542,749, filed on Oct. 3, 2011, provisional application No. 61/467,663, filed on Mar. 25, 2011.

(51) Int. Cl.
| | |
|---|---|
| *A61B 5/00* | (2006.01) |
| *G06F 19/00* | (2018.01) |
| *A61N 1/08* | (2006.01) |
| *G08B 21/18* | (2006.01) |
| *G08B 21/24* | (2006.01) |
| *G16H 40/20* | (2018.01) |
| *G16H 40/67* | (2018.01) |
| *G16H 20/10* | (2018.01) |
| *G16H 50/30* | (2018.01) |
| *A61B 1/00* | (2006.01) |
| *A61M 1/00* | (2006.01) |
| *H04W 4/00* | (2018.01) |
| *A61N 1/39* | (2006.01) |

(52) U.S. Cl.
CPC .......... *G06F 19/00* (2013.01); *G06F 19/3418* (2013.01); *G06F 19/3456* (2013.01); *G08B 21/18* (2013.01); *G08B 21/24* (2013.01); *G16H 20/10* (2018.01); *G16H 40/20* (2018.01); *G16H 40/67* (2018.01); *G16H 50/30* (2018.01); *A61B 1/00* (2013.01); *A61M 1/00* (2013.01); *A61N 1/3925* (2013.01); *H04W 4/00* (2013.01)

(56) References Cited

U.S. PATENT DOCUMENTS

| | | |
|---|---|---|
| 4,576,170 A | 3/1986 | Bradley et al. |
| 4,580,572 A | 4/1986 | Granek et al. |
| 4,583,547 A | 4/1986 | Granek et al. |
| 4,632,122 A | 12/1986 | Johansson et al. |
| 4,729,377 A | 3/1988 | Granek et al. |
| 4,926,879 A | 5/1990 | Sevrain et al. |
| 4,928,690 A | 5/1990 | Heilman et al. |
| 4,978,926 A | 12/1990 | Zerod et al. |
| 4,991,217 A | 2/1991 | Garrett et al. |
| 5,062,834 A | 11/1991 | Gross et al. |
| 5,078,134 A | 1/1992 | Heilman et al. |
| 5,348,008 A | 9/1994 | Bornn et al. |
| 5,365,932 A | 11/1994 | Greenhut |
| 5,381,798 A | 1/1995 | Burrows |
| 5,472,453 A | 12/1995 | Alt |
| 5,544,661 A | 8/1996 | Davis et al. |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,865,736 A | 2/1999 | Baker, Jr. et al. |
| 5,929,601 A | 7/1999 | Kaib et al. |
| 5,944,669 A | 8/1999 | Kaib |
| 6,006,132 A | 12/1999 | Tacker, Jr. et al. |
| 6,016,445 A | 1/2000 | Baura |
| 6,065,154 A | 5/2000 | Hulings et al. |
| 6,097,982 A | 8/2000 | Glegyak et al. |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,336,900 B1 | 1/2002 | Alleckson et al. |
| 6,374,138 B1 | 4/2002 | Owen et al. |
| 6,390,996 B1 | 5/2002 | Halperin et al. |
| 6,406,426 B1 | 6/2002 | Reuss et al. |
| 6,418,346 B1 | 7/2002 | Nelson et al. |
| 6,442,433 B1 | 8/2002 | Linberg |
| 6,546,285 B1 | 4/2003 | Owen et al. |
| 6,602,191 B2 | 8/2003 | Quy |
| 6,681,003 B2 | 1/2004 | Linder et al. |
| 6,690,969 B2 | 2/2004 | Bystrom et al. |
| 6,694,191 B2 | 2/2004 | Starkweather et al. |
| 6,804,554 B2 | 10/2004 | Ujhelyi et al. |
| 6,827,695 B2 | 12/2004 | Palazzolo et al. |
| 6,889,078 B2 | 5/2005 | Struble et al. |
| 6,889,079 B2 | 5/2005 | Bocek et al. |
| 6,908,437 B2 | 6/2005 | Bardy |
| 6,990,373 B2 | 1/2006 | Jayne et al. |
| 7,088,233 B2 | 8/2006 | Menard |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,860,558 B2 | 12/2010 | Feild et al. |
| 7,953,478 B2 | 5/2011 | Vaisnys et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,290,574 B2 | 10/2012 | Feild et al. |
| 8,319,632 B1 | 11/2012 | Vaisnys et al. |
| 8,331,574 B2 | 12/2012 | Powers |
| 8,364,221 B2 | 1/2013 | Mannheimer et al. |
| 8,369,944 B2 | 2/2013 | Macho et al. |
| 8,406,842 B2 | 3/2013 | Kaib et al. |
| 8,644,925 B2 | 2/2014 | Volpe et al. |
| 8,649,861 B2 | 2/2014 | Donnelly et al. |
| 8,676,313 B2 | 3/2014 | Volpe et al. |
| 8,706,215 B2 | 4/2014 | Kaib et al. |
| 8,774,917 B2 | 7/2014 | Macho et al. |
| 8,880,196 B2 | 11/2014 | Kaib |
| 8,897,860 B2 | 11/2014 | Volpe et al. |
| 8,904,214 B2 | 12/2014 | Volpe et al. |
| 9,283,399 B2 | 3/2016 | Donnelly |
| 2001/0031991 A1 | 10/2001 | Russial |
| 2002/0181680 A1 | 12/2002 | Linder et al. |
| 2003/0004547 A1 | 1/2003 | Owen et al. |
| 2003/0032988 A1 | 2/2003 | Fincke |
| 2003/0054866 A1* | 3/2003 | Byers ............... H04W 48/04 455/567 |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0049233 A1 | 3/2004 | Edwards |
| 2005/0049515 A1 | 3/2005 | Misczynski et al. |
| 2005/0131465 A1 | 6/2005 | Freeman et al. |
| 2005/0246199 A1 | 11/2005 | Futch |
| 2006/0015148 A1* | 1/2006 | McCabe ............. A61N 1/3706 607/9 |
| 2006/0036292 A1 | 2/2006 | Smith et al. |
| 2006/0059976 A1 | 3/2006 | Simonenko et al. |
| 2006/0085049 A1 | 4/2006 | Cory et al. |
| 2006/0178706 A1 | 8/2006 | Lisogurski et al. |
| 2006/0211934 A1 | 9/2006 | Hassonjee et al. |
| 2006/0259080 A1 | 11/2006 | Vaisnys et al. |
| 2006/0270952 A1 | 11/2006 | Freeman et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |

(56) References Cited

U.S. PATENT DOCUMENTS

| | | |
|---|---|---|
| 2007/0162075 A1 | 7/2007 | O&pos et al. |
| 2007/0169364 A1 | 7/2007 | Townsend et al. |
| 2007/0197878 A1 | 8/2007 | Shklarski |
| 2007/0232946 A1* | 10/2007 | Feild ................ A61B 5/0424 600/509 |
| 2007/0239220 A1 | 10/2007 | Greenhut et al. |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030309 A1 | 2/2008 | Darrouzet |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0097793 A1 | 4/2008 | Dicks et al. |
| 2008/0249591 A1 | 10/2008 | Gaw et al. |
| 2008/0266118 A1 | 10/2008 | Pierson et al. |
| 2008/0287749 A1 | 11/2008 | Reuter |
| 2008/0306560 A1 | 12/2008 | Macho et al. |
| 2008/0306562 A1 | 12/2008 | Donnelly et al. |
| 2008/0312709 A1 | 12/2008 | Volpe et al. |
| 2009/0018428 A1 | 1/2009 | Dias et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0146822 A1 | 6/2009 | Soliman |
| 2009/0221887 A1 | 9/2009 | Mannheimer et al. |
| 2009/0232286 A1 | 9/2009 | Hurwitz |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0312650 A1 | 12/2009 | Maile et al. |
| 2010/0052892 A1 | 3/2010 | Allen et al. |
| 2010/0056881 A1 | 3/2010 | Libbus et al. |
| 2010/0069735 A1 | 3/2010 | Berkner |
| 2010/0076513 A1 | 3/2010 | Warren et al. |
| 2010/0076533 A1 | 3/2010 | Dar et al. |
| 2010/0234716 A1 | 9/2010 | Engel |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0022105 A9 | 1/2011 | Owen et al. |
| 2011/0080294 A1 | 4/2011 | Tanishima et al. |
| 2011/0170692 A1 | 7/2011 | Konrad et al. |
| 2011/0172550 A1 | 7/2011 | Martin et al. |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0126975 A1* | 5/2012 | Gonzales ................ G08B 29/20 340/540 |
| 2012/0146797 A1 | 6/2012 | Oskin et al. |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0259377 A1 | 10/2012 | Freeman |
| 2012/0283794 A1 | 11/2012 | Kaib et al. |
| 2012/0289809 A1 | 11/2012 | Kaib et al. |
| 2012/0293323 A1 | 11/2012 | Kaib et al. |
| 2012/0302860 A1 | 11/2012 | Volpe et al. |
| 2013/0013014 A1 | 1/2013 | Donnelly et al. |
| 2013/0060149 A1 | 3/2013 | Song et al. |
| 2013/0085538 A1 | 4/2013 | Volpe et al. |
| 2013/0144355 A1 | 6/2013 | Macho et al. |
| 2013/0218252 A1 | 8/2013 | Kaib et al. |
| 2013/0231711 A1 | 9/2013 | Kaib |
| 2013/0324868 A1 | 12/2013 | Kaib et al. |
| 2013/0325078 A1 | 12/2013 | Whiting |
| 2013/0325096 A1 | 12/2013 | Dupelle et al. |
| 2014/0004814 A1 | 1/2014 | Elghazzawi |
| 2014/0031885 A1 | 1/2014 | Elghazzawi et al. |
| 2014/0163334 A1 | 6/2014 | Volpe et al. |
| 2014/0206974 A1 | 7/2014 | Volpe et al. |
| 2014/0277243 A1 | 9/2014 | Maskara et al. |
| 2014/0303680 A1 | 10/2014 | Donnelly et al. |
| 2014/0324112 A1 | 10/2014 | Macho et al. |
| 2015/0035654 A1 | 2/2015 | Kaib et al. |
| 2015/0039042 A1 | 2/2015 | Amsler et al. |
| 2015/0039053 A1 | 2/2015 | Kaib et al. |
| 2015/0080699 A1 | 3/2015 | Kaib et al. |
| 2015/0224330 A1 | 8/2015 | Kaib et al. |

FOREIGN PATENT DOCUMENTS

| | | |
|---|---|---|
| EP | 0335356 | 8/1990 |
| EP | 0761255 | 3/1997 |
| EP | 1720446 | 11/2006 |
| EP | 1455640 | 1/2008 |
| JP | 5115450 | 5/1993 |
| JP | H10505515 | 6/1998 |
| JP | 2002509472 | 3/2002 |
| JP | 2002-514107 | 5/2002 |
| JP | 2006091013 | 4/2006 |
| JP | 2007522859 | 8/2007 |
| JP | 2008-302228 | 12/2008 |
| JP | 2008302225 | 12/2008 |
| JP | 2009510631 | 3/2009 |
| JP | 2009-521865 | 6/2009 |
| JP | 2009536068 | 10/2009 |
| WO | 83/04171 | 12/1983 |
| WO | 1998039061 | 9/1998 |
| WO | 2000002484 | 1/2000 |
| WO | 2004054656 | 7/2004 |
| WO | 2004078259 | 9/2004 |
| WO | 2005082454 | 9/2005 |
| WO | 2006050325 | 5/2006 |
| WO | 2007019325 | 2/2007 |
| WO | 2009034506 | 3/2009 |
| WO | 2009122277 | 10/2009 |
| WO | 2010025432 | 3/2010 |
| WO | 2010077997 | 7/2010 |
| WO | 2012006524 | 1/2012 |
| WO | 2012100219 | 7/2012 |
| WO | 2013130957 | 9/2013 |
| WO | 2014018160 | 1/2014 |
| WO | 2014097035 | 6/2014 |

OTHER PUBLICATIONS

DeBock, et al., "Captopril treatment of chronic heart failure in the very old," J. Gerontol. (1994) 49: M148-M152.

http://web.archive.org/web/20030427001846/http:/www.lifecor.comiimagelib/imageproduct.asp. Published by LifeCor, Inc., 2002, on a webpage owned by LifeCor, Inc.

O'Keeffe et al., "Reproducability and responsiveness of quality of life assessment and six minute walk test in elderly heart failure patients," Heart (1998) 80: 377-382.

International Search Report and Written Opinion from corresponding PCT Application No. PCT/US2012/030428, dated Nov. 7, 2012.

Association for the Advancement of Medical Instrumentation, ANSI/AAMI DF80:2003 Medical Electrical Equipment—Part 2-4: Par-

(56) References Cited

OTHER PUBLICATIONS ticular Requirements for the Safety of Cardiac Defibrillators (including Automated External Defibrillators) 2004, ISBN 1-57020-210-9; abstract; p. vi; p. 50, section 107.1.2.

ZOLL Medical Corporation, LifeVest Model WCD 3000 Operator's Manual, Pittsburgh, PA.

* cited by examiner

SYSTEM AND METHOD FOR ADAPTING ALARMS IN A WEARABLE MEDICAL DEVICE

RELATED APPLICATIONS

This application claims benefit under 35 U.S.C. § 120 as a continuation of U.S. patent application Ser. No. 15/483,203, titled "SYSTEM AND METHOD FOR ADAPTING ALARMS IN A WEARABLE MEDICAL DEVICE," filed on Apr. 10, 2017. U.S. patent Ser. No. 15/483,203 claims benefit under 35 U.S.C. § 120 as a continuation of U.S. patent application Ser. No. 15/159,557, titled "SYSTEM AND METHOD FOR ADAPTING ALARMS IN A WEARABLE MEDICAL DEVICE," filed on May 19, 2016. U.S. patent application Ser. No. 15/159,557 claims benefit under 35 U.S.C. § 120 as a continuation of U.S. patent application Ser. No. 14/704,033, titled "SYSTEM AND METHOD FOR ADAPTING ALARMS IN A WEARABLE MEDICAL DEVICE," filed on May 5, 2015. U.S. patent application Ser. No. 14/704,033 claims benefit under 35 U.S.C. § 120 as a continuation of U.S. patent application Ser. No. 13/428,703, titled "SYSTEM AND METHOD FOR ADAPTING ALARMS IN A WEARABLE MEDICAL DEVICE," filed on Mar. 23, 2012. U.S. patent application Ser. No. 13/428,703 claims benefit under 35 U.S.C. § 119(e) to U.S. Provisional Application Ser. No. 61/467,663, titled "SYSTEM AND METHOD FOR ADAPTING ALARMS IN A WEARABLE MEDICAL DEVICE," filed on Mar. 25, 2011. U.S. patent application Ser. No. 13/428,703 also claims benefit under 35 U.S.C. § 119(e) to U.S. Provisional Application Ser. No. 61/542,749, titled "SYSTEM AND METHOD FOR ADAPTING ALARMS IN A WEARABLE MEDICAL DEVICE," filed on Oct. 3, 2011. Each of application Ser. Nos. 15/483,203, 15/159,557, 14/704,033, 13/428,703, 61/542,749, and 61/467,663 is hereby incorporated herein by reference in its entirety.

BACKGROUND

Technical Field

Aspects of the present invention relate to medical devices, and more particularly to apparatus and methods for adapting alarms in medical devices.

Discussion of Related Art

Some wearable medical devices notify patients wearing the medical device of events of interest to the patient. In certain situations, wearable medical devices receive responses to these notifications from the patient. For instance, a wearable defibrillator worn by an ambulatory patient generates an alarm if the patient's electrocardiogram (ECG) signal indicates a cardiac abnormality. Where the ECG signal indicates that the cardiac abnormality is treatable via a therapeutic shock, the wearable defibrillator must receive a response to this notification if the patient wishes to avoid the administration of an unnecessary therapeutic shock.

In situations where the cause of a notification is not as pressing, a wearable medical device may repeatedly notify a patient of the event of interest. For example, if a battery installed in the wearable medical device is running low on power, the wearable medical device may notify the patient. After a period of time, if the wearable medical device continues to detect that the battery has a low power state, the wearable medical device may reissue the previous notification. However, in the case of a critical care medical device, such as the LifeVest® Wearable Cardioverter Defibrillator available from Zoll Medical Corporation of Chelmsford, Mass., lack of a responsive action by the patient may result in the wearable defibrillator becoming inoperative due to lack of battery power.

SUMMARY

Examples disclosed herein adapt the characteristics of an alarm issued by a wearable medical device to increase the efficacy of a wearable medical device while maintaining or enhancing the usage experience of patients wearing the medical device. For instance, some adaptations presented herein increase the probability that patients will respond to the alarm in a suitable manner. Other adaptations tailor alarms to fit the traits and preferences of particular patients. Thus, various examples address situations in which a patient does not hear an alarm, does not recognize the significance of an alarm or does not respond according to established timetables.

In one example, a method for adapting alarms issued by a wearable medical device is provided. The method includes acts of issuing a first instance of an alarm; determining that no predetermined response to the first instance of the alarm was received within a target response time; adapting, responsive to determining that no predetermined response was received within the target response time, at least one characteristic of the alarm according to an adaptation path associated with the alarm and issuing a second instance of the alarm, the second instance of the alarm having the at least one adapted characteristic.

In the method, the act of determining that the first instance of the alarm was not effective may include receiving no response within a target response time. In addition, the act of adapting the at least one characteristic of the alarm may include increasing the intensity of the alarm. Further, the act of adapting the at least one characteristic of the alarm may include changing the conduit of the alarm. The act of changing the conduit of the alarm may include transmitting the alarm to a personal electronic device. Moreover, the method may further operate using an alarm profile that indicates an alarm that is triggered upon occurrence of an event. Additionally, the method may further include acts of storing within the alarm profile, responsive to adapting the at least one characteristic of the alarm, an association between the alarm and the adaptation path; detecting an occurrence of the event; identifying, responsive to detecting the occurrence of the event, the association between the alarm and the adaptation path; adapting, responsive to identifying the association, at least one characteristic of the alarm according to the adaptation path and issuing a third instance of the alarm, the third instance of the alarm having the at least one adapted characteristic.

According to another example, a method for adapting alarms issued by a wearable medical device is provided. The method includes acts of receiving an alarm profile via an interface, the alarm profile indicating an alarm to be triggered upon occurrence of an event and including an association between an adaptation path and the alarm; detecting an occurrence of the event; identifying, responsive to detecting the occurrence of the event, the association between the adaptation path and the alarm; adapting, responsive to identifying the association, at least one characteristic of the alarm according to the adaptation path; and issuing an instance of the alarm having the at least one adapted characteristic.

According to another example, a wearable medical device controller is provided. The wearable medical device controller includes a memory storing alarm profile information and a processor coupled to the memory. The processor being configured to issue a first instance of an alarm, determine that no predetermined response to the first instance of the alarm was received within a target response time, adapt, responsive to determining that no predetermined response was received within the target response time, at least one characteristic of the alarm according to an adaptation path associated with the alarm and issue a second instance of the alarm, the second instance of the alarm having the at least one adapted characteristic. In addition, the processor may be configured to determine that the first instance of the alarm was not effective where the processor receives no response within a target response time.

According to another example, a method for adapting alarms issued by a wearable medical device is provided. The method includes acts of detecting an inhibiting factor associated with an alarm and adapting, responsive to detecting the inhibiting factor, at least one characteristic of the alarm according to an adaptation path.

According to another example, a method for adapting alarms issued by a wearable medical device is provided. The method includes acts of detecting a correlation between a value of an independent variable and an alarm response pattern associated with a patient, determining, after detecting the correlation, that the independent variable has the value and adapting, responsive to determining that the independent variable has the value, an alarm based on the alarm response pattern.

According to another example, a wearable medical device controller is provided. The device controller includes a memory and a processor coupled to the memory. The processor is configured to determine a correlation between a phenomenon identifiable by the wearable medical device controller and at least one response pattern associated with a patient and store, responsive to detecting the correlation, an adaptation path to address the at least one response pattern, the adaptation path specifying an adaptation of at least one characteristic of an alarm. The at least one response pattern may include a plurality of response patterns and the adaptation path may reflect adaptations made to address at least some of the plurality of response patterns.

In the device controller, the processor may be further configured to detect the phenomenon and adapt, responsive to detecting the phenomenon, the at least one characteristic of the alarm according to the adaptation path. The processor may be configured to determine the correlation by determining a correlation between a value of an independent variable indicative of the phenomenon and the at least one response pattern. Adapting the at least one characteristic of the alarm may include increasing the intensity of the alarm. Adapting the at least one characteristic of the alarm may include changing the conduit of the alarm. Changing the conduit of the alarm may include transmitting the alarm to a personal electronic device. In some examples, the phenomenon may be an inhibiting factor.

In the device controller, the memory may store an alarm profile indicating that the alarm be triggered upon occurrence of an event. The alarm profile may include an association between the adaptation path and the alarm. The processor may be further configured to detect an occurrence of the event and issue a first instance of the alarm, the first instance having the at least one adapted characteristic. The adaptation path may specify a plurality of adaptations and the processor is further configured to determine that no predetermined response to the first instance of the alarm was received within a target response time; adapt, responsive to determining that no predetermined response was received within the target response time, a characteristic of the alarm according to an adaptation from the plurality of adaptations and issue a second instance of the alarm, the second instance of the alarm having the adapted characteristic.

The device controller may further comprise an interface in data communication with the processor. The processor may be further configured to receive the alarm profile via the interface and store the alarm profile in the memory. The processor may be further configured to receive a new adaptation path via the interface and store the new adaptation path in the alarm profile.

According to another example, a wearable medical device controller is provided. The device controller includes a memory and a processor coupled to the memory. The memory stores an alarm profile indicating that an alarm be triggered upon occurrence of an event and includes an association between an adaptation path and the alarm. The processor is configured to detect an occurrence of the event; issue a first instance of the alarm; determine that no predetermined response to the first instance of the alarm was received within a target response time; adapt, responsive to determining that no predetermined response was received within the target response time, at least one characteristic of the alarm according to the adaptation path; and issue a second instance of the alarm, the second instance of the alarm having the at least one adapted characteristic.

According to another example, a method for adapting alarms issued by a wearable medical device is provided. The method includes acts of determining, by the wearable medical device, a correlation between a phenomenon identifiable by the wearable medical device and at least one response pattern associated with a patient and storing, responsive to detecting the correlation, an adaptation path to address the at least one response pattern, the adaptation path specifying an adaptation of at least one characteristic of an alarm. The act of determining the correlation includes determining the correlation between the phenomenon and a plurality of response patterns and storing the adaptation path includes storing an adaptation path that reflects adjustments made to address at least some of the plurality of response patterns.

The method may further comprise acts of detecting the phenomenon and adapting, responsive to detecting the phenomenon, the at least one characteristic of the alarm according to the adaptation path. In the method, the act of determining the correlation may include an act of determining a correlation between a value of an independent variable indicative of the phenomenon and the at least one response pattern. The act of adapting the at least one characteristic of the alarm may include ac act of increasing the intensity of the alarm. The act of adapting the at least one characteristic of the alarm may include changing the conduit of the alarm. The act of changing the conduit of the alarm may include an act of transmitting the alarm to a personal electronic device.

The method may further comprise act of detecting an occurrence of an event and issuing a first instance of the alarm, the first instance having the adaptation of the at least one characteristic of the alarm. The adaptation path may specify a plurality of adaptations and the method further comprises acts of determining that no predetermined response to the first instance of the alarm was received within a target response time; adapting, responsive to determining that no predetermined response was received within the target response time, a characteristic of the alarm according to an adaptation from the plurality of adaptations and issuing a second instance of the alarm, the second instance of the alarm having the adapted characteristic.

Still other aspects, examples, and advantages of these exemplary aspects and examples, are discussed in detail below. Moreover, it is to be understood that both the foregoing information and the following detailed description are merely illustrative examples of various aspects, and are intended to provide an overview or framework for understanding the nature and character of the claimed subject matter. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in that example and other examples. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Aspects and examples disclosed herein relate to apparatus and processes for adapting alarms issued by a wearable medical device. The examples disclosed herein are potentially applicable to a wide variety of wearable medical devices. In some examples, the wearable medical devices are configured in accord with the wearable medical devices described in co-pending application Ser. No. 13/109,382, entitled WEARABLE AMBULATORY MEDICAL DEVICE WITH MULTIPLE SENSING ELECTRODES, filed May 17, 2011, which is incorporated by reference herein in its entirety. In other examples, the wearable medical device is a monitoring device that does not conduct a therapy delivery method or include a therapy delivery apparatus. In each of these examples, a control unit of the wearable medical device includes a set of components configured to perform the adaptation processes described herein. This set of components may include hardware components or a combination of hardware and software components.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Wearable Medical Device Controller

Figure 1:
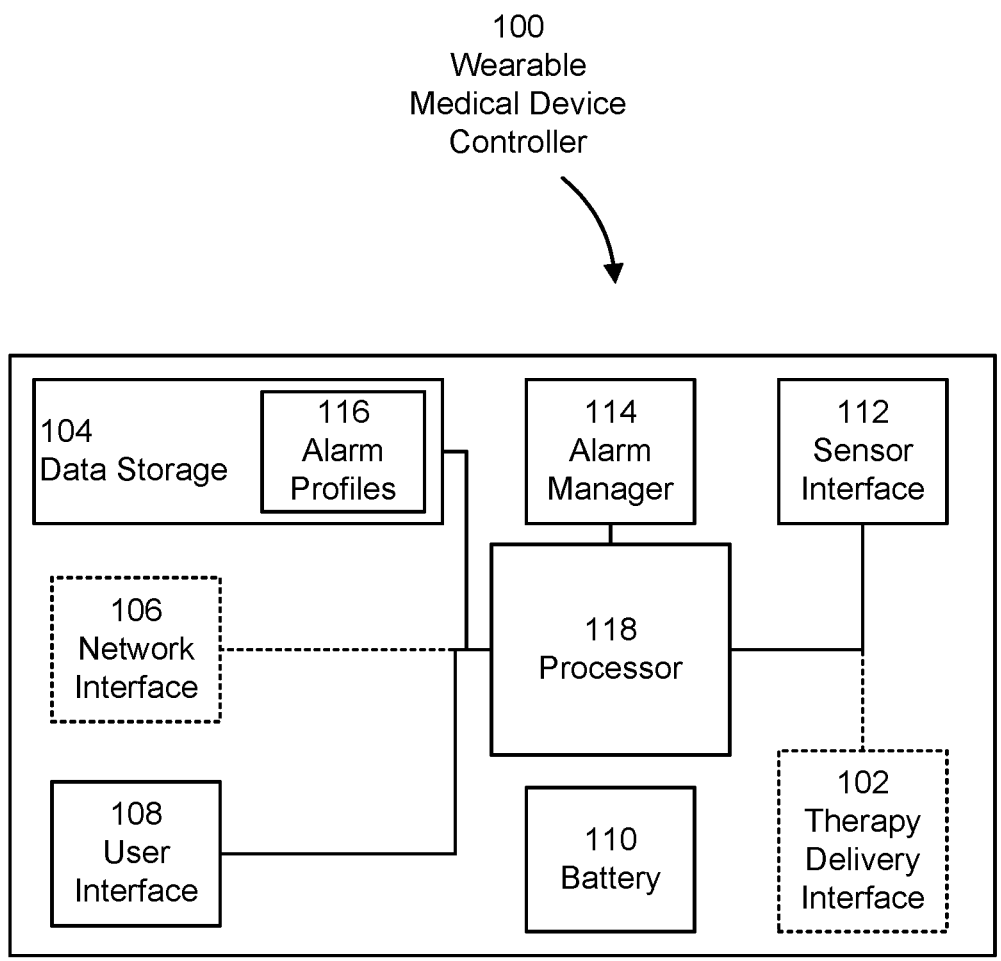
FIG. 1 is a functional schematic of one example of a wearable medical device controller.

FIG. 1 illustrates a wearable medical device controller 100 that is configured to monitor a patient and the patient's environment for events of interest and to adapt notifications reporting these events. As shown in FIG. 1, the wearable medical device controller 100 includes a processor 118, a sensor interface 112, an alarm manager 114, a therapy delivery interface 102, data storage 104, a communication network interface 106, a user interface 108 and a battery 110. The data storage 104 includes alarm profile information 116. Further, in this illustrated example, the battery 110 is a rechargeable 3 cell 2200 mAh lithium ion battery pack that provides electrical power to the other device components with a minimum 24 hour runtime between charges.

According to the example illustrated in FIG. 1, the processor 118 is coupled to the sensor interface 112, the therapy delivery interface 102, the data storage 104, the network interface 106 and the user interface 108. The processor 118 performs a series of instructions that result in manipulated data which is stored in and retrieved from the data storage 104. According to a variety of examples, the processor 118 is a commercially available processor such as a processor manufactured by Texas Instruments, Intel, AMD, Sun, IBM, Motorola, Freescale and ARM Holdings. However, the processor 118 may be any type of processor, multiprocessor or controller, whether commercially available or specially manufactured. For instance, according to one example, the processor 118 may include a power conserving processor arrangement such as described in co-pending application Ser. No. 12/833,096, entitled SYSTEM AND METHOD FOR CONSERVING POWER IN A MEDICAL DEVICE, filed Jul. 9, 2010 (hereinafter the "'096 application"), which is incorporated by reference herein in its entirety. In another example, the processor 118 is an Intel® PXA270.

In addition, in several examples the processor 118 is configured to execute a conventional RTOS, such as RTLinux. In these examples, the RTOS may provide platform services to application software, such as some examples of the alarm manager 114 which is discussed further below. These platform services may include inter-process and network communication, file system management and standard database manipulation. However, one of many operating systems may be used, and examples are not limited to any particular operating system or operating system characteristic. For instance, in some examples, the general purpose processor 118 may be configured to execute a non-real time operating system, such as BSD or GNU/Linux.

The alarm manager 114 is configured to manage alarm profiles, such as the alarm profile information 116, and notify one or more intended recipients of events specified within the alarm profiles as being of interest to the intended recipients. These intended recipients may include external entities such as users (patients, physicians, and monitoring personnel) as well as computer systems (monitoring systems or emergency response systems). The alarm manager 114 is also configured to adapt notifications according to an adaptation path specified within the alarm profile information 116. Adaptation paths are discussed further below with reference to the alarm profile information 116.

The alarm manager 114 may be implemented using hardware or a combination of hardware and software. For instance, in one example, the alarm manager 114 is implemented as a software component that is stored within the data storage 112 and executed by the processor 118. In this example, the instructions included in the alarm manager 114 program the processor 118 to configure alarm profiles and notify intended recipients using the alarm profiles. In other examples, alarm manager 114 may be an application-specific integrated circuit (ASIC) that is coupled to the processor 118 and tailored to manage alarm profiles and notify intended recipients using alarms specified within the alarm profiles. Thus, examples of alarm manager 114 are not limited to a particular hardware or software implementation. Particular examples of the processes performed by the alarm manager 114 are discussed further below with reference to FIGS. 2-5 and the Example Alarm Adaptations section below.

In some examples, the components disclosed herein, such as the alarm manager 114, may read parameters that affect the functions performed by the components. These parameters may be physically stored in any form of suitable memory including volatile memory, such as RAM, or non-volatile memory, such as a magnetic hard drive. In addition, the parameters may be logically stored in a proprietary data structure, such as a database or file defined by a user mode application, or in a commonly shared data structure, such as an application registry that is defined by an operating system. In addition, some examples provide for both system and user interfaces, as may be implemented using the user interface 108, that allow external entities to modify the parameters and thereby configure the behavior of the components.

For example, the alarm manager 114 includes an alarm mode parameter. The alarm mode parameter indicates a generalized set of preferences that the alarm manager 114 applies to triggered alarms. The alarm manager 114 may adjust any characteristics of an alarm depending on the particular alarm mode currently in effect. Example alarm modes include, but are not limited to, normal (no modification to alarm characteristics), silent (do not produce sensory output to one or more senses when reporting the alarm), loud (increase sensory output to one or more senses when reporting the alarm), vehicle (decrease sensory output and target response times, delay alarms with adaptation paths indicating to delay the alarm if the alarm mode parameter indicates vehicle mode, issue triggered alarms through an in-vehicle communications and entertainment system if available), walking (issue triggered alarms via an output embedded within an article of clothing, such as a foot buzzer), and personal electronic device (issue triggered alarms via a personal electronic device such as an earpiece, phone, tablet computing device, pen, personal entertainment device, sport equipment, personal digital assistant, etc. . . . ).

The data storage 104 includes a computer readable and writeable nonvolatile data storage medium configured to store non-transitory instructions and other data. In addition, the data storage 104 includes a processor memory that stores data during operation of the processor 118. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 118 causes data to be read from the nonvolatile data storage medium into the processor memory prior to processing the data. In these examples, the processor 118 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 104 may include executable programs or other code that can be executed by the processor 118. The data storage 104 also may include information that is recorded, on or in, the medium, and this information may be processed by the processor 118 during execution of instructions. More specifically, the information may be stored in one or more data structures specifically configured to conserve storage space or increase data exchange performance. The instructions may be persistently stored as encoded signals, and the instructions may cause the processor 118 to perform the functions described herein. The medium may, for example, be optical disk, magnetic disk or flash memory, among others, and may be permanently affixed to, or removable from, the wearable medical device controller 100.

The alarm profile information 116 includes data used by the alarm manager 114 to notify intended recipients of events of interest. More particularly, according to the illustrated example, the alarm profile information 116 includes information that identifies events of interest, characteristics of one or more alarms used to report the identified events and one or more adaptation paths for each of the one or more alarms. Events of interest may include any event detectable by the wearable medical device controller 100. However, in broad terms, events of interest may be categorized as concerning the patient wearing the wearable medical device, such as an indication of a physiological abnormality in the patient, or concerning the wearable medical device itself, such as a component in need of service (for example, a low battery).

Common alarm characteristics include an alarm identifier, an intended recipient of the alarm, one or more potential responses, a conduit through which the alarm is provided, content for the alarm, an intensity with which the content is communicated, an issuance rate at which the content is communicated and a target response time. The conduits through which alarms may be issued include, among others, the user interface 108, the network interface 106 and the therapy delivery interface 102. Adaptation paths may specify initial characteristics of alarms and how the characteristics of the alarms are altered based on the currently selected alarm mode, the number of times the alarms have issued, the circumstances surrounding the intended recipients of any alarms and any responsive actions taken, or not taken, by the external entities. In general, the adaptations specified by adaptation paths involve actions such as increasing the intensity with which an alarm is communicated, altering the content or conduit of an alarm and increasing the issuance rate with which an alarm is communicated. Specific examples of adaptation paths that are specified with the alarm profile information 116 and that the alarm manager 114 is configured to conduct are discussed further below within the Example Alarm Adaptations section.

As illustrated in FIG. 1, the alarm manager 114 and the alarm profile information 116 are separate components. However, in other examples, the alarm manager 114 and the alarm profile information 116 may be combined into a single component or re-organized so that a portion of the data included in the alarm manager 114, such as executable code that causes the processor 118 to adapt a triggered alarm, resides in the alarm profile information 118, or vice versa. Such variations in these and the other components illustrated in FIG. 1 are intended to be within the scope of the examples disclosed herein.

The alarm profile information 116 may be stored in any logical construction capable of storing information on a computer readable medium including, among other structures, flat files, indexed files, hierarchical databases, relational databases or object oriented databases. In addition, various examples organize the alarm profile information 116 into particularized and, in some cases, unique structures to perform the functions disclosed herein. In these examples, the data structures are sized and arranged to store values for particular types of data.

As shown in FIG. 1, the wearable medical device controller 100 includes several system interface components 102, 106 and 112. Each of these system interface components is configured to exchange, i.e. send or receive, data with one or more specialized devices that may be located within the wearable medical device controller 100 or elsewhere. The components used by the interfaces 102, 106 and 112 may include hardware components, software components or a combination of both. In the instance of each interface, these components physically and logically couple the wearable medical device controller 100 to the specialized devices. This physical and logical coupling enables the wearable medical device controller 100 to both communicate with and, in some instances, control the operation of the specialized devices. These specialized devices may include physiological sensors, therapy delivery devices and computer networking devices.

According to various examples, the hardware and software components of the interfaces 102, 106 and 112 employ a variety of coupling and communication techniques. In some examples, the interfaces 102, 106 and 112 use leads, cables or other wired connectors as conduits to exchange data between the wearable medical device controller 100 and specialized devices. In other examples, the interfaces 102, 106 and 112 communicate with specialized devices using wireless technologies such as radio frequency or infrared technology. The software components included in the interfaces 102, 106 and 112 enable the processor 118 to communicate with specialized devices. These software components may include elements such as objects, executable code and populated data structures. Together, these software components provide software interfaces through which the processor 118 can exchange information with specialized devices. Moreover, in at least some examples where one or more specialized devices communicate using analog signals, the interfaces 102, 106 and 112 further include components configured to convert analog information into digital information, and vice versa, to enable the processor 118 to communicate with specialized devices.

As discussed above, the system interface components 102, 106 and 112 shown in the example of FIG. 1 support different types of specialized devices. For instance, the components of the sensor interface 112 couple the processor 118 to one or more physiological sensors such as a body temperature sensors, respiration monitors, and dry capacitive ECG electrodes, one or more environmental sensors such as atmospheric thermometers, airflow sensors, video sensors, audio sensors, accelerometers, GPS locators, and hygrometers. In these examples, the sensors may include sensors with a relatively low sampling rate, such as wireless sensors.

The components of the therapy delivery interface 102 couple one or more therapy delivery devices, such as capacitors and defibrillator electrodes, to the processor 118. In addition, the components of the network interface 106 couple the processor 118 to a computer network via a networking device, such as a bridge, router or hub. According to a variety of examples, the network interface 106 supports a variety of standards and protocols, examples of which include USB (via, for example, a dongle to a computer), TCP/IP, Ethernet, Wireless Ethernet, Bluetooth, Zig-Bee, M-Bus, CAN-bus, IP, IPV6, UDP, DTN, HTTP, FTP, SNMP, CDMA, NMEA and GSM. To ensure data transfer is secure, in some examples, the wearable medical device controller 100 can transmit data via the network interface 106 using a variety of security measures including, for example, TLS, SSL or VPN. In other examples, the network interface 106 includes both a physical interface configured for wireless communication and a physical interface configured for wired communication. According to various embodiments, the network interface 106 enables communication between the wearable medical device controller 100 and a variety of personal electronic devices including computer enabled glasses and earpieces.

Thus, the various system interfaces incorporated in the wearable medical device controller 100 allow the device to interoperate with a wide variety of devices in various contexts. For instance, some examples of the wearable medical device controller 100 are configured to perform a process of sending critical events and data to a centralized server via the network interface 106. An illustration of a process in accord with these examples is disclosed in U.S. Pat. No. 6,681,003, entitled "DATA COLLECTION AND SYSTEM MANAGEMENT FOR PATIENT-WORN MEDICAL DEVICES" and issued on Jan. 20, 2004 which is hereby incorporated by reference in its entirety.

As illustrated in FIG. 1, the therapy delivery interface 102 and the network interface 106 are optional and may not be included in every example. For instance, a heart rate monitor may employ the wearable medical device controller 100 to issue adaptive alarms but may not include a therapy delivery interface 102 to treat cardiac abnormalities. Similarly, a wearable defibrillator may include the wearable medical device controller 100 to provide adaptive alarm functionality but may not include a network interface 106 where, for example, the wearable defibrillator is designed to rely on the user interface 108 to announce alarms.

The user interface 108 shown in FIG. 1 includes a combination of hardware and software components that allow the wearable medical device controller 100 to communicate with an external entity, such as a user. These components are configured to receive information from actions such as physical movement, verbal intonation or thought processes. In addition, the components of the user interface 108 can provide information to external entities. Examples of the components that may be employed within the user interface 108 include keyboards, mouse devices, trackballs, microphones, electrodes, touch screens, printing devices, display screens and speakers. In some examples, the electrodes include an illuminating element, such as an LED. In other examples, the printing devices include printers capable of rendering visual or tactile (Braille) output.

The wearable medical device controller 100 has a variety of potential applications and is well suited to devices that notify external entities of a variety of events, some of which require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the wearable medical device controller 100 is well suited include critical care medical devices, such as a wearable external defibrillator. An example of one such defibrillator is described in the '096 application with reference to FIG. 3. In at least one example, the wearable defibrillator 300 illustrated in FIG. 3 of the '096 application employs the wearable medical device controller 100, as disclosed in the present application, as a substitute for the portable treatment controller 200 described in the '096 application. In this example, the ECG Electrodes and Therapy Pads illustrated in FIG. 3 of the '096 application are logically and physically coupled to the wearable medical device controller 100 via the sensor interface 112 and the therapy delivery interface 102, respectively.

Alarm Adaptation Processes

Figure 2:
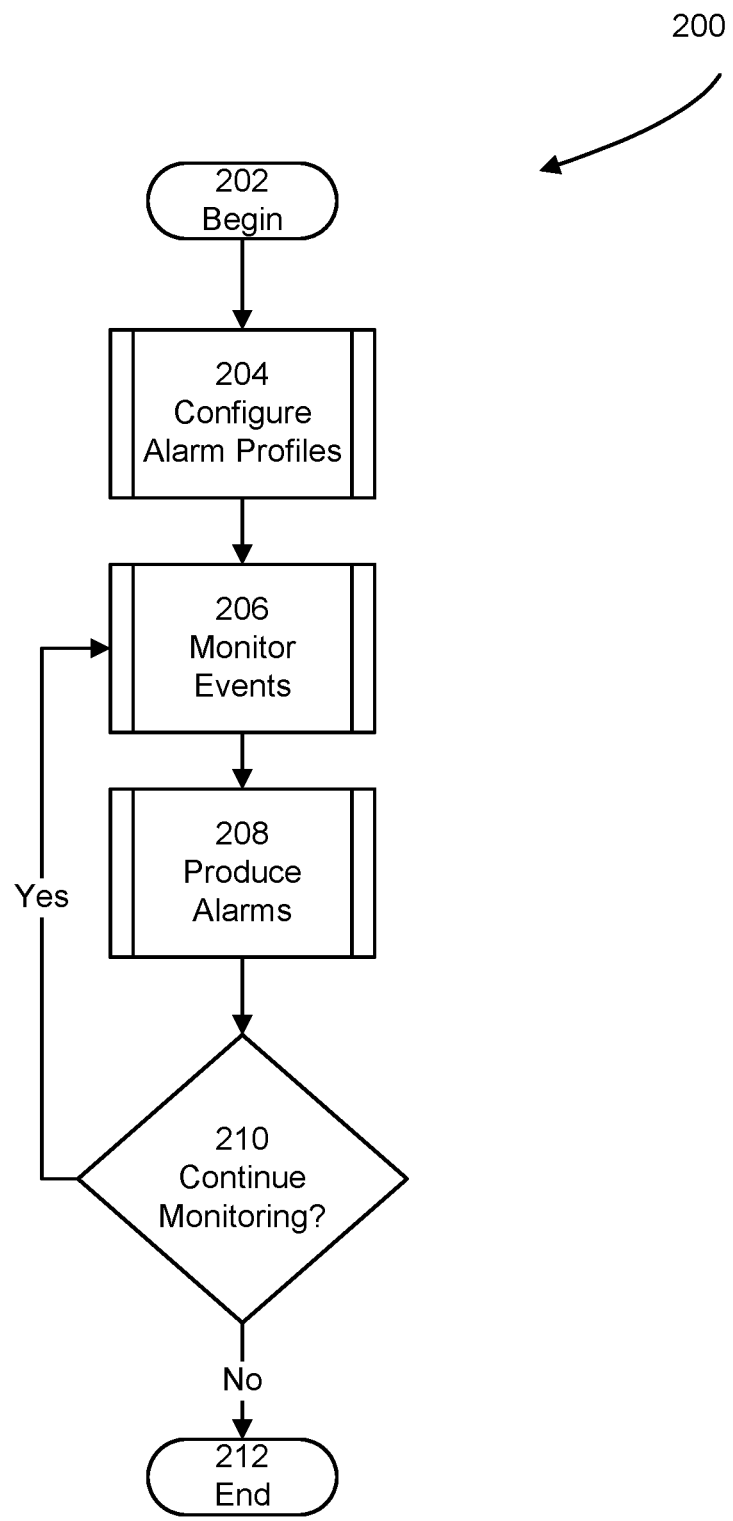
FIG. 2 is a flow diagram of one example of a process for adapting alarms issued by a medical device.

Various examples provide processes through which a medical device adapts alarms that report events of interest to one or more intended recipients. In these examples, the medical device is arranged to include the wearable medical device controller 100 and performs the acts disclosed herein, including the acts described in the Example Alarm Adaptations section below. FIG. 2 illustrates one such process 200 that includes acts of configuring alarm profiles, monitoring events and producing alarms. Process 200 begins at 202.

In act 204, the medical device configures alarm profile information. According to some examples, an alarm manager, such as the alarm manager 114, implements a configuration interface through which the alarm manager receives alarm profile information from a user, such as a patient, physician or equipment technician. Acts in accord with these examples are discussed below with reference to FIG. 3.

In act 206, the medical device monitors events. According to a variety of examples, the alarm manager monitors the various inputs of the medical device for events of interest as specified in alarm profile information, such as the alarm profile information 116. Acts in accord with these examples are discussed below with reference to FIG. 4.

In act 208, the medical device produces an alarm. According to various examples, the alarm manager adapts and issues the alarm in accord with the alarm profile information. Acts in accord with these examples are discussed below with reference to FIG. 5.

In act 210, the medical device determines if an interruption in monitoring is about to commence, such as an interruption caused by shutdown of the wearable medical device controller. If so, the medical device proceeds to 212. Otherwise the medical device returns to act 206.

Process 200 ends at 212. Examples in accord with process 200 allow a medical device to notify intended recipients, such as the patient, a physician or monitoring personnel, of important events in a manner that decreases the likelihood that the alarm will be ignored. Thus, such examples increase the efficacy of the medical device.

Figure 3:
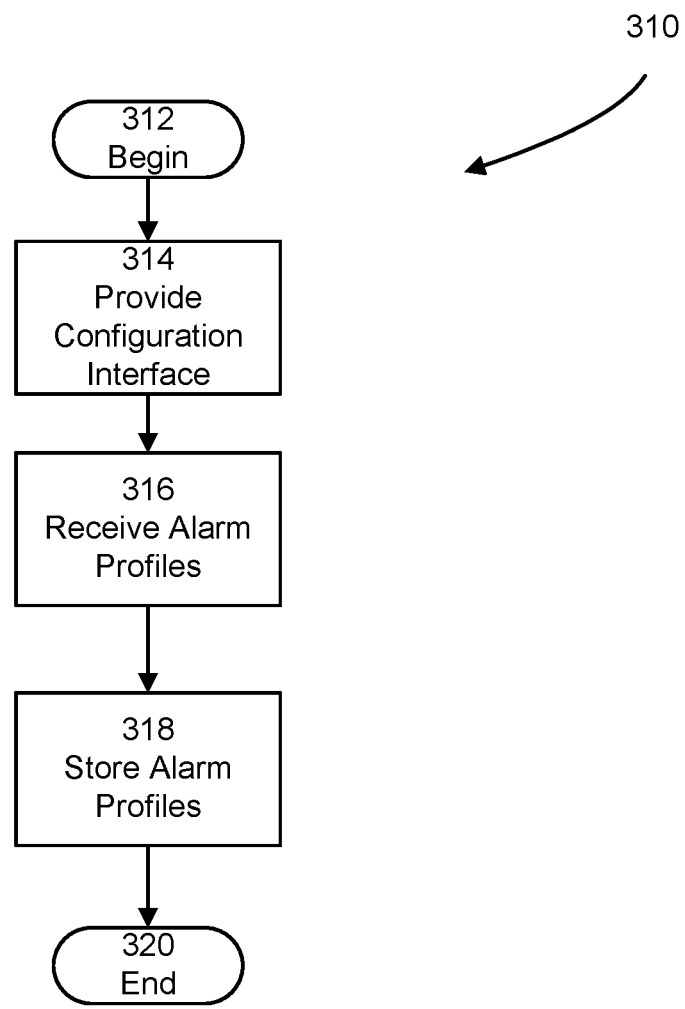
FIG. 3 is a flow diagram of one example of a process for configuring information within an alarm profile.

As discussed above with regard to act 204 shown in FIG. 2, various examples provide processes for configuring alarm profiles by a medical device. FIG. 3 illustrates one such process 310 that implements act 204 and that includes acts of providing a configuration interface, receiving alarm profile information and storing the alarm profile information. A medical device implementing process 310 begins at 312.

In act 314, an alarm manager, such as the alarm manager 114, provides a configuration interface through which the alarm manager receives alarm profile information, such as the alarm profile information 116. The characteristics of the configuration interface vary from example to example. For instance, in one example, the configuration interface presents, via the user interface 108, one or more screens arranged to receive information identifying an alarm, an intended recipient of the alarm, one or more potential responses, a conduit through which the alarm is provided, content for the alarm, an intensity with which the content is communicated, an issuance rate with which the content is communicated, a target response time and an adaptation path for the alarm. According to another example, the configuration interface includes a system interface implemented via a network interface, such as the network interface 106, and through which the alarm manager receives alarm profile information from an external system. In one example, the external system is a web site through which external entities, such as patients or monitoring personnel, may configure alarm profile information for download to the wearable medical device controller. Other examples detailing characteristics of the configuration interface provided are discussed below in the Example Alarm Adaptations section.

In act 316, the alarm manager receives alarm profile information via the configuration interface. For instance, in one example, the configuration interface receives an intended recipient of the alarm, one or more potential responses, a conduit through which the alarm is provided, content for the alarm, an intensity with which the content is communicated, an issuance rate with which the content is communicated, a target response time and an adaptation path for the alarm via the screens described above. In another example, the alarm profile information is received from the external system described above. In act 318, the alarm manager stores the alarm profile information in data storage, such as the data storage 104. A medical device implementing process 310 terminates the process at 320. Examples in accord with process 310 enable medical devices to gather alarm profile information for later use in reporting and adapting alarms.

Figure 4:
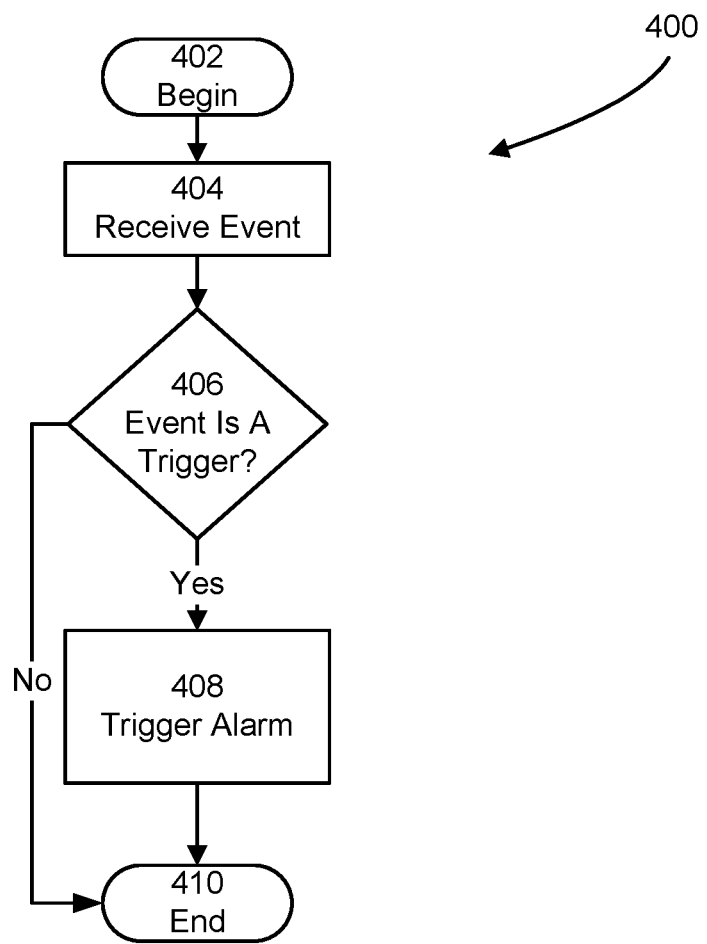
FIG. 4 is a flow diagram of one example of a process for monitoring events associated with a medical device.

As discussed above with regard to act 206 shown in FIG. 2, various examples provide processes for monitoring events encountered in a medical device. FIG. 4 illustrates one such process 400 that may be used to implement act 206 and that includes acts of receiving event information, determining if the event triggers an alarm, and triggering an alarm. A medical device implementing process 400 begins at 402.

In act 404, an alarm manager, such as the alarm manager 114, receives an event from the processor 118. In act 406, the alarm manager determines if the event triggers an alarm by referencing alarm profile information, such as the alarm profile information 116. If so, the alarm manager triggers the alarm in act 408. Otherwise the alarm manager proceeds to 410. A medical device implementing process 400 terminates the process at 410. Examples in accord with process 400 enable medical devices to determine if an event encountered by the device triggers an alarm.

Figure 5:
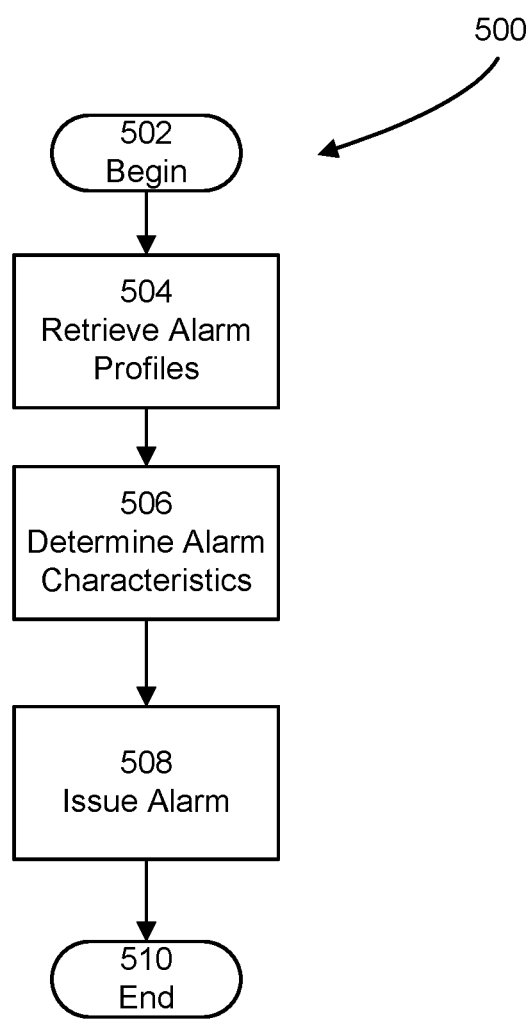
FIG. 5 is a flow diagram of one example of a process for producing alarms associated with a medical device.

As discussed above with regard to act 208 shown in FIG. 2, various examples provide processes for producing alarms by medical devices. FIG. 5 illustrates one such process 500 that may be used to implement act 208 and that includes acts of retrieving alarm profiles, determining alarm characteristics and issuing an alarm. A medical device implementing process 500 begins at 502.

In act 504, an alarm manager, such as the alarm manager 114, retrieves alarm profile information, such as the alarm profile information 116, from a data storage, such as the data storage 104. In act 506, the alarm manager determines the alarm characteristics based on the alarm profile information and the alarm mode parameter. In one example, the alarm manager determines if the alarm has previously been issued but no predetermined response has been received. If this is the situation, the alarm manager adapts the alarm according to the adaptation path associated with the alarm. Further, in some examples, the alarm manager may record this adaptation so that future instances of the alarm are adapted automatically, i.e. without requiring the issuance of an ineffective alarm. In another example, the alarm manager determines, prior to issuing any alarm instances, that an alarm profile indicates instances of the alarm should be adapted according to the adaptation path and the alarm manager adapts the alarm accordingly. In another example, the alarm manager determines if the environment of the intended recipient of the alarm is such that the alarm should be adapted and, if so, adapts the alarm according to the adaptation path associated with the alarm. Other examples detailing characteristics and adaptations of alarms are discussed below in the Example Alarm Adaptations section.

In act 508, the alarm manager issues the alarm with the characteristics as determined in act 506. A medical device implementing process 500 terminates the process at 510. Examples in accord with process 500 enable medical devices to issue alarms that are adapted to effectively notify the intended recipient of the alarm. This, in turn, increases the likelihood that the intended recipient will perform any actions required to suitably respond to the alarm, thereby benefiting the wearer of the medical device.

Each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein.

Example Alarm Adaptations

According to various examples, an alarm manager, such as the alarm manager 114, performs a wide variety of actions with reference to adaptation paths specified in alarm profile information, such as the alarm profile information 116. For instance, in some examples, the alarm manager receives, via a configuration interface as discussed above, an adaptation path specifying that the alarm manager should initially issue an alarm via one or more conduits and later, if necessary, adapt the alarm to different or multiple conduits. These conduits may communicate, or cause other devices to communicate, with the intended recipient via different sensory outputs such as optical (a display, LED, illuminated electrode, etc. . . . ), auditory (a speaker), and tactile (vibrating output) outputs. In at least one example, the adaptation path specifies that the alarm be initially issued as a vibration alarm and subsequently be adapted to a voice instruction using a voice selected by a user via the configuration interface. According to these examples, the alarm manager issues the alarm according to the adaptation path when the alarm is triggered by an event.

In other examples, the alarm manager receives, via the configuration interface, an adaptation path specifying a duration threshold for the amount of time an alarm may be silenced by an external entity. In these examples, the adaptation path further specifies that the alarm manager should, if the alarm is silenced beyond the threshold and no responsive action has been taken, adapt the alarm by increasing the intensity or issuance rate of the alarm or by changing the conduit through which the alarm is communicated. According to these examples, the alarm manager issues the alarm according to the adaptation path when the alarm is triggered by an event. Further, according to one example, the alarm manager adapts, in accord with information specified in the adaptation path, the alarms silenced beyond the threshold by changing the alarm from a tone to a voice command requesting that the intended recipient take a particular action.

In other examples, the alarm manager receives, via the configuration interface, an adaptation path specifying that if no response is received from an external entity within a specified response time, the alarm manager should increase the intensity of an alarm, for example increase the volume in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should change the content of an alarm, for example change from a tone to a voice command in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the issuance rate with which an alarm is being reported, for example decrease the duration between re-issuances of the alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the sensory output through which an alarm is being reported, for example change from auditory to visual indicia or vice versa. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the content of an alarm, for example change from a gentle gong to an ear-piercing siren in the case of an auditory alarm. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should modify the conduit through which an alarm is reported, for example change the reporting device from the wearable medical device controller to another device associated with the intended recipient. These other devices may include personal electronic devices (such as smart phones, PDAs, wired and wireless headphones or headsets, and tablet computing devices), computer systems (through which alarms may be reported via, for example, on-screen pop-ups), home base stations, bedside radios, televisions (through which alarms may be reported, for example, via on-screen pop-ups or widgets), cars or any other addressable device with an output. According to these examples, the alarm manager issues the alarm according to the adaptation path when the alarm is triggered by an event.

In other examples, the alarm manager receives, via the configuration interface, an adaptation path specifying that the alarm manager issue an alarm to a device other than the wearable medical device prior to issuing the alarm to the wearable medical device. For instance, in one example, the adaptation path specifies that the alarm manager issue an alarm via a call to an intended recipient's phone. In another example, the adaptation path specifies that the alarm manager issue an alarm through a Bluetooth headset paired with the wearable medical device. In still another example, the adaptation path specifies that the alarm manager issue an alarm via a text message sent to the intended recipient's phone. In all of these examples, if a response is not received by the wearable medical device within a target response time, the alarm manager issues the alarm via the wearable medical device.

As with other adaptation paths, this adaptation path may be configured to apply to one or more specific events of interest. For example, where the event of interest is detection of a misplaced or improperly attached electrode, the adaptation path may specify that the alarm manager first issue an alarm specifying the color of the misplaced or improperly attached electrode. Alternatively, this adaptation path may specify that the alarm manager first issue an alarm by illuminating an LED included within the misplaced or improperly attached electrode. In another example, the adaptation path may specify that the alarm manager also issue an alarm via the user interface that specifies the color of the electrode. In another example where the event of interest is passage of a threshold amount of time since a battery included within the wearable medical device has been replaced, the adaptation path may specify that the alarm manager first issue an alarm by sending a text to the phone of an intended recipient.

In other examples, the alarm manager receives, via the configuration interface, an adaptation path specifying that if no response is received from an external entity within a specified response time, the alarm manager should modify the intended recipient to a list of intended recipients including, for example, family members of a patient or local emergency response personnel. According to these examples, the alarm manager issues the alarm according to the adaptation path when the alarm is triggered by an event.

In other examples, the alarm manager receives, via the configuration interface, an adaptation path specifying that if no response is received from an external entity within a specified response time, the alarm manager should, prior to each issuance of an alarm, iterate one or more characteristics of the alarm through a set of values, thereby altering the characteristics of the alarm each time it is issued. This iteration may cycle through the values and may modify any of the characteristics of the alarm including the intensity, issuance rate, content and conduit of the alarm. According to these examples, the alarm manager issues the alarm according to the adaptation path when the alarm is triggered by an event.

In other examples, the alarm manager adjusts the target response time for one or more alarms based on the average patient response time to the alarms. For instance, if the alarm manager detects that the average response time plus a predefined acceptable margin is less than the target response time, the alarm manager may modify the target response time to be equal to the average response time plus the predefined margin.

In other examples, the alarm manager determines, prior to issuance of an alarm, if factors exist that may inhibit the intended recipient's (or bystander's) ability to recognize the alarm. Exemplary inhibiting factors include environmental characteristics, such as excessive sensory stimulation, patient characteristics, such as the physical, mental or emotional state of the patient, and characteristics affecting the wearable medical device. Where an inhibiting factor is present, the alarm manager adapts the alarm to increase the likelihood that the alarm will be recognized despite the presence of the inhibiting factor. Such adaptations may include extending the target response time by some predetermined amount, adjusting the intensity of the alarm or both. In the case of an audio alarm, adjusting the intensity may include adjusting the amplitude or the frequency of the alarm. In other examples, the alarm manager detects the amount of motion or the ambient noise level of the environment of the intended recipient to determine if these factors may be inhibiting recognition of the alarm. According to these examples, the alarm manager extends the target response time or adjusts the intensity of the alarm upon determining that the motion or the ambient noise level is above a predetermined threshold.

In other examples, the alarm manager determines, via a hygrometer such as the hygrometer described above, the relative humidity of the current environment of the wearable medical device and alters the audio alarm characteristics to be more tolerant of the environmental conditions. For instance, in these examples, the alarm manager may increase the target response time or increase the volume of an audio alarm to compensate for the relatively high sound absorption present in a high humidity environment.

In other examples, the alarm manager determines whether the wearable medical device is properly fitted to the patient. In these examples, if the alarm manager determines that the wearable medical device is not properly fitted, the alarm manager adapts alarms to overcome this inhibiting factor. For instance, the alarm manager may increase the intensity of a tactile alarm to increase the likelihood that a patient wearing a loose-fitting medical device feels the tactile alarm. Alternatively, the alarm manager may change the tactile alarm to an auditory alarm.

In another example, the alarm manager uses audio input or physiological data to determine if the mood or stress level of the patient may be an inhibiting factor or may affect the patient's response to an alarm. In this example, where the intended recipient appears to be undergoing stress, the alarm manager decreases the intensity or the duration of the alarm to prevent panic or some other negative or volatile reaction to the alarm. In another instance, where the patient appears to be lying in response to an alarm, the alarm manager repeats the alarm or alters the alarm to verify the veracity of the response. Other adaptations may be performed in response to alarm inhibiting factors and examples are not limited to particular adaptation paths or inhibiting factors.

Some wearable medical devices are continuously or nearly continuously worn by patients for extended periods of time. In fact, in certain situations, these periods of time can extend to two months or more. Over these extended time periods, some patients repeatedly display particularized alarm response patterns. For instance, a patient who commutes to work in the morning, takes lunch at midday, commutes home in the evening and sleeps at night may display a repeatedly delayed response pattern at particular points during the day, such as during the morning and evening commutes, or when the patient is asleep.

According to various examples, the alarm manager analyzes alarm response data for repeating patterns and adapts alarms issued according to an adaptation path that addresses the repeating pattern. More particularly, in some of these examples, the alarm manager identifies the number of false alarms (e.g. alarms responded to by canceling treatment) that occur over a period of time. In these examples, the alarm manager compares the number of false alarms to a threshold value. If the number of false alarms exceeds the threshold value, the alarm manager reports this event to the patient and provides the patient with a set of corrective actions specific to the type of false alarm encountered.

In other examples, the alarm manager determines correlations between values of independent variables that represent a phenomenon and a tendency for a patient to respond to alarms in a particular way (i.e., follow a particular alarm response pattern). This phenomenon may be any phenomenon quantifiable and identifiable by the wearable medical device via sensors or other facilities disclosed herein. Examples of identifiable phenomenon include one or more events as described herein, a predetermined series of events occurring over a predefined span of time, a physical circumstance, such as the time of day, and physiological measurements. According to some examples, the alarm manager may determine correlations by analyzing information describing alarms and responses to alarms as this information is processed by the wearable medical device. The alarm manager may periodically scan a history of this alarm response data that is compiled by the alarm manager during its normal operation. In one example, the alarm manager scans the history of alarm response patterns daily, while in another example, the alarm manager performs this analysis on a weekly or monthly basis. It is to be appreciated that, in some of these examples, the alarm manager determines correlations from population samples that vary in size and whose values are recorded over an extended period of time. Thus, in these examples, the correlations reflect multiple, discrete alarms and response episodes.

In some examples, the alarm manager identifies one or more correlations of interest between independent variables and patient response patterns. In one example, the alarm manager identifies interesting correlations by determining that a value of a correlation exceeds a predetermined threshold. In other examples, the alarm manager automatically creates one or more alarm profiles for each interesting correlation. In these examples, the alarm manager stores one or more adaptation paths within the automatically created alarm profiles. These adaptation paths specify adaptations that address the correlated patient response pattern (i.e., adaptations to alarm characteristics that improve the efficacy of the alarm). Some specific examples of the adaptations performed by the alarm manager when implementing these adaptation paths are described further below. It is to be appreciated that, in some examples, the alarm manager iteratively adjusts the adaptation path correlated with the patient response pattern over an extended period of time. In these examples, the adaptation path gradually improves as the alarm manager analyzes an increasing number of discrete alarms and response episodes.

The alarm manager may adapt alarms to accommodate a repeating pattern in a variety of ways. For instance, to accommodate a period of time in which the patient is normally slow to respond, the alarm manager may simply extend the target response time for any alarms issued. Alternatively, if the alarm is of sufficient importance, the alarm manager may increase the intensity of the alarm or change the conduit used to communicate the alarm. In another example, to accommodate a physiological indication that is correlated with delayed response times by a patient (such as an indication exhibited by the patient during sleep), the alarm manager may delay issuance of the alarm until the physiological indication changes. Examples of the alarm manager may determine correlations between independent variables, other than time of day or physiological data, and alarm response patterns, examples of which are not limited to a particular set of independent variables or alarm response patterns.

In other examples, the alarm manager determines if acuity (or lack of acuity) of the patient's senses may be an inhibiting factor and, if so, adapts alarms to overcome these obstacles. For instance, in one example, the alarm manager administers, within the configuration interface, a hearing test. In this example, the results of the hearing test are stored in the alarm profile information and used by the alarm manager to tailor the audio alarms to a specified frequency, amplitude and tonal qualities. Further, according to this example, the alarm manager issues the audio alarms according to the frequency, amplitude and tonal settings when the audio alarms are triggered by an event. The adaptations in this example enable the alarms to be perceived by the intended recipients with partial hearing loss. In another example designed to address hearing loss, the alarm manager alters the conduit through which audio alarms are presented, instead presenting the alarms as visual alarms through a display.

In other examples, the alarm manager receives, via the configuration interface, an indication that the patient possesses impaired sight. In these examples, the alarm manager alters the conduit through which visual alarms are presented to a non-visual conduit. Non-visual conduits include an auditory conduit (e.g., a speaker) or a tactile conduit (vibration or Braille printout). Alarms issued through a vibrating tactile conduit may simply vibrate once, vibrate repeatedly or vibrate according to a signature pattern, such as Morse code.

In other examples, the alarm manager receives, via the configuration interface, an adaptation path specifying that if no response is received from an external entity within a specified response time, the alarm manager should determine if any bystanders are near the intended recipient. In these examples, the adaptation path may further specify that where bystanders are detected, the alarm manager should adjust the content of the alarm to direct it to the bystanders. In one example, the alarm manager detects the presence of bystanders by determining a difference between a detected voice pattern and a sample voice pattern of the intended recipient that is stored in the alarm profile information. According to these examples, the alarm manager issues the alarm according to the adaptation path when the alarm is triggered by an event.

In other examples, the alarm manager determines that the patient may be asleep and, in response, increases alarm intensities and target response times. In these examples, the alarm manager determines that the patient may be asleep by analyzing any combination of a variety of factors including: physiological data (such as heart rate and respiration), the current time of day, and the presence (or lack) of patient motion, the body position of the patient and the proximity of the patient to a home base station near the patient's bed. In one example, the home base station is configured in accord with the base unit described in co-pending application Ser. No. 13/286,533, entitled REMOTE DEVICE ALARM, filed Nov. 1, 2011, which is incorporated by reference herein in its entirety. Further the alarm manager may receive, via the configuration interface, an adaptation path that specifies a multi-stage alarm in which an intense, initial "wake-up" alarm is followed by a separate alarm reporting the event of interest with different intensity and content. Alternatively, the adaptation path may specify that alarms should be routed to a home base station so that the triggered alarms are communicated with greater intensity. According to these examples, the alarm manager issues the alarm according to the adaptation path when the alarm is triggered by an event.

In other examples, the alarm manager determines that the patient may be mentally or physically impaired and, in response, directs the alarm to another intended recipient, such as a doctor, relative or other caregiver. In these examples, the alarm manager determines that the patient may be mentally impaired by analyzing any combination of a variety of factors including: physiological data (such as heart rate and respiration), the presence (or lack) of patient motion, and audio input (to determine if the patient's speech is impaired).

In other examples, the alarm manager receives, via the configuration interface, an adaptation path that specifies that when the patient fails to take medication according to a prescribed schedule, the alarm manager issues an alarm reminding the patient to do so. In these examples, the alarm manager determines that the patient failed to take medication by analyzing physiological data (such as heart rate and respiration) or by questioning the patient via the user interface. In some of these examples, particular patterns in the physiological data may be linked to particular medications and these links may be used to provide specific alarms to the patient. For instance, if the physiological data exhibits a pattern indicative of congestive heart failure and that pattern is linked to lisinopril, the alarm manager may issue an alarm to remind the patient to take a prescribed dose of lisinopril.

In other examples, the alarm manager receives, via the configuration interface, an adaptation path that specifies adjustments of the intensity, issuance rate or duration of an alarm based on the severity of the event of interest. For instance, in some examples in which the wearable medical device controller is incorporated into a wearable defibrillator, the adaptation path may define particular alarm characteristics to indicate the number and type of electrodes that are not properly positioned on the patient's body. In one example, the adaptation path may specify different tones to indicate incorrect positioning for ECG electrodes and therapy pads. Similarly, in this example, the adaptation path may specify increasing alarm intensities to indicate increasing numbers of electrodes being out of position. According to these examples, the alarm manager issues the alarm according to the adaptation path when the alarm is triggered by an event.

In other examples, the alarm manager is trained by the patient, via the configuration interface, to detect one or more locations, such as a car, office or home, frequently visited by the patient. In one of these examples, the alarm manager receives a location identifier from a user via the configuration interface, records and stores information representative of the ambient noise within the location and creates and stores an association between the location and the stored ambient noise information. In another of these examples, the alarm manager receives a location identifier from a user via the configuration interface, records and stores information representative of the current GPS position of the wearable medical device controller and creates and stores an association between the location and the current GPS position. According to these examples, the alarm manager automatically detects the location of the wearable medical device controller, sets the alarm mode parameter to a value associated with the location and adjusts the triggered alarms accordingly (both according to the alarm mode parameter in general and as defined by the adaptation paths associated with the alarms).

In a particular example, where the alarm mode parameter indicates the patient is occupying a vehicle, the alarm manager issues, via the network interface 106, alarms to the patient through an in-vehicle communications and entertainment system, such as OnStar, SYNC, MyFord Touch, BMW Assist and Lexus Link, that allows users to make hands-free telephone calls and control music and other functions using voice commands. In this example, the alarm manager provides an interface to the patient via the in-vehicle communications and entertainment system. In addition, according to this example, the alarm manager may employ the facilities of the in-vehicle communications system to issue notifications to intended recipients other than the patient, for example sending a request for help to monitoring or emergency personnel.

According to another example, where the alarm mode parameter indicates the patient is at home, the alarm manager issues, via the network interface 106, alarms to the patient through a home security system that allows users to make hands-free telephone calls and control functions using voice command or through a television or computer located within the home of the patient. In this example, the alarm manager provides an interface to the patient via the home security system, television or computer. In addition, according to this example, the alarm manager may employ the facilities of the home security system to issue notifications to intended recipients other than the patient, for example sending a request for help to monitoring or emergency personnel.

According to another example, where the alarm mode parameter indicates the patient is using a personal electronic device, the alarm manager issues, via the network interface 106, alarms to the patient through the personal electronic device. In this example, the alarm manager provides an interface to the patient via the personal electronic device. In addition, according to this example, the alarm manager may employ the facilities of the personal electronic device to issue notifications to intended recipients other than the patient, for example sending a request for help to monitoring or emergency personnel. Moreover, the alarm manager may preempt the normal functioning of the personal electronic device when issuing alarms. For instance, where the personal electronic device is being used to make a phone call, the alarm manager may send alarms and messages into the phone so they can be heard from an external entity. In another example, the personal electronic device may include a light, buzzer or some other sensory output that is activated by the alarm manager when the alarm manager issues an alarm.

In yet another example, a sensory output, such as a light, is positioned within the field of vision of a patient by being integrated into a pair of glasses that are worn by the patient. According to this example, the alarm manager activates the light when issuing an alarm, thereby notifying the patient of the alarm.

In other examples, the alarm manager provides a user interface, via the user interface 108, that receives and responds to voice commands. According to this example, the alarm manager validates the identity of the speaker by verifying that the voice pattern matches a voice pattern stored in data storage, such as the data storage 104. Further, according to this example, the configuration interface receives and responds to voice commands and allows external entities, such as the patient or monitoring personnel to configure alarm information using voice commands.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A system comprising:
   an ambulatory medical device comprising
      at least one sensor configured to acquire electrocardiogram (ECG) signals from a patient;
      a network interface configured to communicate wirelessly with an electronic device distinct from the ambulatory medical device;
      a user interface;
      a memory storing alarm information specifying one or more alarms and one or more conduits through which the one or more alarms are to be provided; and
      at least one processor coupled to the memory, the network interface, the user interface, and the at least one sensor and configured to
         monitor ECG data based on the ECG signals to detect a cardiac abnormality in the patient
         identify, based on the alarm information, an alarm of the one or more alarms triggered by the cardiac abnormality;
         adapt, based on the alarm information, the alarm to output via at least one conduit of the one or more conduits, the one or more conduits comprising
            the network interface configured to communicate wirelessly with the electronic device, and
            the user interface of the ambulatory medical device; and
      the electronic device, the electronic device being configured to receive the alarm; and
         issue the alarm.

2. The system of claim 1, wherein the electronic device comprises one or more of an earpiece, a smart phone, a tablet computing device, an article of clothing, and in-vehicle entertainment system, and a home security system.

3. The system of claim 1, wherein the ambulatory medical device further comprises a therapy delivery interface coupled to the at least one processor and the at least one processor is further configured to adapt, based on the alarm information, the alarm to issue via the therapy delivery interface.

4. The system of claim 1, wherein to adapt the alarm comprises to change the at least one conduit to comprise the network interface, the user interface, or both the network interface and the user interface.

5. The system of claim 4, wherein to change the one or more conduits comprises to transmit the alarm to the electronic device via the network interface.

6. The system of claim 5, wherein the electronic device comprises an earpiece and to issue the alarm comprises to issue an alarm via the earpiece.

7. The system of claim 5, wherein the electronic device comprises an article of clothing and to issue the alarm comprises to issue an alarm via the article of clothing.

8. The system of claim 5, wherein the electronic device comprises an in-vehicle entertainment system and to issue the alarm comprises to issue an alarm via the in-vehicle entertainment system.

9. The system of claim 5, wherein the electronic device comprises a personal electronic device and to issue the alarm comprises to issue an alarm via the personal electronic device.

10. The system of claim 9, wherein the personal electronic device comprises a smart phone and to issue the alarm via the personal electronic device comprises to issue an alarm via the smart phone.

11. The system of claim 9, wherein the the personal electronic device comprises a smart phone and to issue the alarm via the personal electronic device comprises to place a phone call or send a text message.

12. The system of claim 9, wherein to issue the alarm via the personal electronic device comprises to preempt normal functioning of the personal electronic device.

13. The system of claim 9, wherein the personal electronic device comprises a smart phone and to preempt normal functioning of the personal electronic device comprises to send an alarm via an active phone call.

14. The system of claim 9, wherein the the personal electronic device comprises a tablet computing device and to issue the alarm via the personal electronic device to issue an alarm via the tablet computing device.

15. The system of claim 5, wherein the electronic device comprises a display and to issue the alarm comprises to issue an alarm via the display.

16. The system of claim 5, wherein the electronic device comprises a home security system and to issue the alarm comprises to issue an alarm via the home security system.

17. The system of claim 5, wherein the at least one sensor is coupled to a light emitting diode and the at least one processor is configured to issue the alarm via the light emitting diode.

18. A method of adapting alarms in an ambulatory medical device, comprising:

storing, in a memory of the ambulatory medical device, alarm information specifying one or more alarms and one or more conduits through which the one or more alarms are to be provided;

acquiring electrocardiogram (ECG) signals from a patient coupled to the ambulatory medical device;

monitoring ECG data based on the ECG signals to detect a cardiac abnormality in the patient;

identifying, based on the alarm information stored in the memory of the ambulatory medical device, an alarm of the one or more alarms triggered by the cardiac abnormality;

adapting, based on the alarm information stored in the memory of the ambulatory medical device, the alarm to output via at least one conduit of the one or more conduits, the one or more conduits comprising a network interface configured to communicate wirelessly with an electronic device and a user interface of the ambulatory medical device;

receiving the alarm at the electronic device via the network interface of the ambulatory medical device; and issuing the alarm via the electronic device.

19. The method of claim 18, wherein adapting the alarm comprises selecting the at least one conduit to output the alarm to be at least one of the network interface, the user interface, or both the network interface and the user interface.

20. The method of claim 18, wherein the electronic device comprises a smart phone and issuing the alarm comprises issuing an alarm via the smart phone.

* * * * *

UNITED STATES PATENT AND TRADEMARK OFFICE
CERTIFICATE OF CORRECTION

PATENT NO. : 10,269,227 B2
APPLICATION NO. : 15/965287
DATED : April 23, 2019
INVENTOR(S) : Thomas E. Kaib, Shane S. Volpe and John G. Clark Page 1 of 1

It is certified that error appears in the above-identified patent and that said Letters Patent is hereby corrected as shown below:

In the Claims

Column 21, Line 64, in Claim 1, add --;-- after patient

Column 22, Line 47, in Claim 11, remove "the" after wherein

Column 22, Line 58, in Claim 14, remove "the" after wherein

Signed and Sealed this
Fifteenth Day of October, 2019

Andrei Iancu
*Director of the United States Patent and Trademark Office*